United States Patent [19]

Zech

[11] Patent Number: 5,686,302
[45] Date of Patent: Nov. 11, 1997

[54] DEVICE FOR REMOVING SPERM CELLS FORM SEMINAL FLUID

[76] Inventor: Josef Zech, Brennerstrasse 15, A-6020 Innsbruck, Austria

[21] Appl. No.: 500,953

[22] PCT Filed: Feb. 9, 1994

[86] PCT No.: PCT/AT94/00014
§ 371 Date: Aug. 8, 1995
§ 102(e) Date: Aug. 8, 1995

[87] PCT Pub. No.: WO94/17742
PCT Pub. Date: Aug. 18, 1994

[30] Foreign Application Priority Data

Feb. 9, 1993 [AT] Austria .................... 225/93
Oct. 8, 1993 [AT] Austria .................... 2019/93

[51] Int. Cl.$^6$ ............................ C12M 1/22
[52] U.S. Cl. .................... 435/305.2; 435/288.5; 435/308.1; 422/102
[58] Field of Search ............ 435/2, 287.5, 288.1–288.5, 435/304.1, 304.2, 305.1–305.3, 308.1, 806; 422/101, 102, 99

[56] References Cited

U.S. PATENT DOCUMENTS

| 2,665,237 | 1/1954 | Strawinski | 435/287.5 |
| 3,864,962 | 2/1975 | Stark et al. | 73/55 |
| 4,294,931 | 10/1981 | Levin et al. | 435/288.5 |
| 4,759,344 | 7/1988 | Wang | 435/2 |
| 4,824,247 | 4/1989 | True et al. | 356/244 |
| 5,047,331 | 9/1991 | Swaine et al. | 435/287.5 |
| 5,296,375 | 3/1994 | Kricka et al. | 435/288.5 |

FOREIGN PATENT DOCUMENTS

| 2 539 628 | 7/1984 | France . | |
| 2-31670 | 2/1990 | Japan | 435/288.5 |
| 2 220 003 | 12/1989 | United Kingdom . | |
| 91/06624 | 5/1991 | WIPO | 435/305.2 |

Primary Examiner—William H. Beisner
Attorney, Agent, or Firm—Wenderoth, Lind & Ponack

[57] ABSTRACT

A device for separating sperm cells from seminal fluid includes a first container for accepting the seminal fluid and a second container for accepting sperm cells separated from the seminal fluid. At least one wall separates interiors of the first and second containers, and such wall has an upper edge. A bridge member of U-shaped cross-sectional configuration is positioned to fit over and enclose the upper edge and an upper portion of the wall to define therewith a gap that forms a fluid bridge through which sperm cells that have separated from the seminal fluid may pass from the interior of the first container to the interior of the second container.

12 Claims, 2 Drawing Sheets

5,686,302

DEVICE FOR REMOVING SPERM CELLS FORM SEMINAL FLUID

BACKGROUND OF THE INVENTION

The invention relates to a device for obtaining sperm cells from seminal fluid, with a first container for accepting the seminal fluid and a second container for accepting the sperm cells separated from the seminal fluid, whereby both containers are interconnected when the seminal fluid is covered with a nutrient solution.

For artificial insemination, sperm cells are usually separated out of seminal fluid before they are brought into contact with an egg cell in vitro or in utero. Through this separation step, the sperm cells can be damaged.

A device for in vitro fertilization with a container for the egg cells and a container for the seminal fluid has already been proposed, whereby the containers are interconnected when egg cells and seminal fluid are covered with nutrient fluid. The problem with this practically untested device is that the fluid bridge between the two containers is formed simply by a part of the nutrient fluid which extends over an upper edge of an inner of the containers (which accepts egg cells). Especially when such container is moved, e.g., when being put under a microscope, the nutrient fluid splashes between the parts of the container so that the movement of the sperm do not determine, but rather outside influences determine, which of the sperm cells lead to insemination. Multiple insemination cannot be eliminated.

SUMMARY OF THE INVENTION

The invention aspires to approximate natural behaviors as much as possible. While avoiding damaging separation steps, such as centrifuging, preferably the most mobile sperm should be admitted for insemination.

In accordance with the invention, a fluid bridge is provided between the containers, the cross-section of which is limited by solid walls.

BRIEF DESCRIPTION OF THE DRAWINGS

Other objects, features and advantages of the present invention will be apparent from the following detailed description taken with the accompanying drawings, wherein.

DETAILED DESCRIPTION OF THE INVENTION

Figure 1:
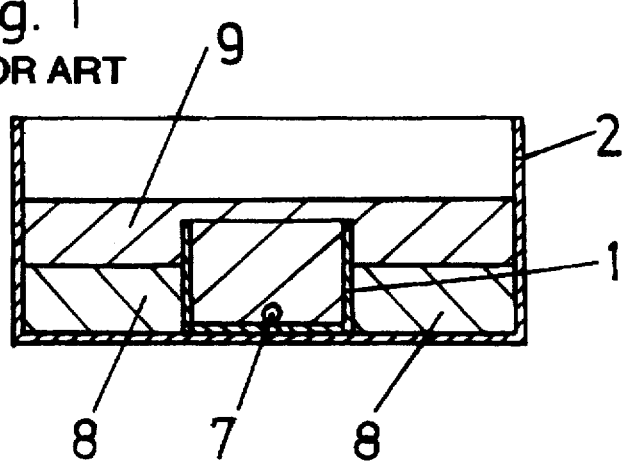
FIG. 1 is a schematic cross-sectional view of a prior art device.

A known device in accordance with FIG. 1 comprises a container 2 for accepting seminal fluid 8, in which a container 1 for accepting separated sperm cells is arranged. If one covers the seminal fluid 8 with nutrient solution 9, then the individual sperm cells reach the nutrient solution. The transport of the sperm cells to an egg cell 7 does not take place, however, through the movement of the sperm cells, but also through the macroscopic flow of the nutrient solution.

Figure 2:
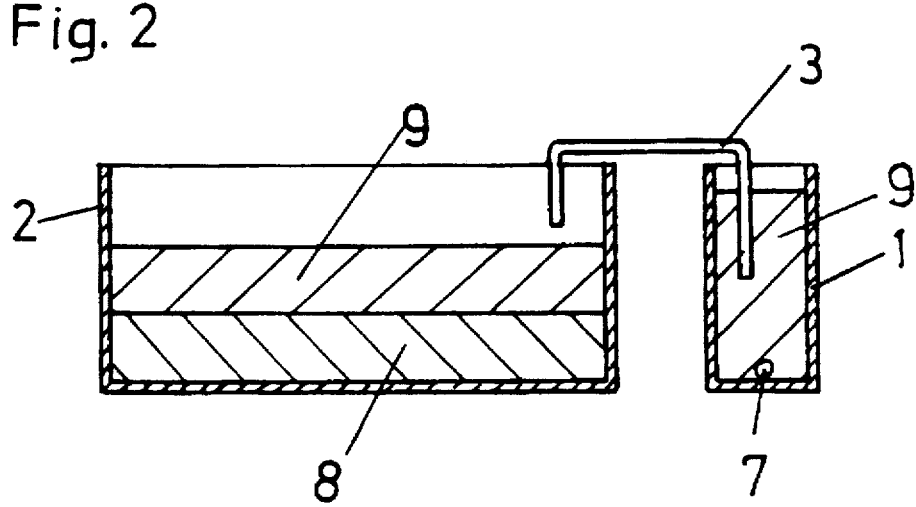
FIGS. 2–5 are similar views illustrating various embodiments of the device of the present invention.

In accordance with the invention, containers 1 and 2 are connected with one another only by a conduit, in which no significant flow takes place. The conduit is defined by solid walls that are spaced, e.g., by a distance of between 0.1 mm and 1 mm. A bridge piece which is hollow inside can be used between the two containers 1 and 2 as the conduit, particularly designed as small capillary pipes in the exemplary embodiment in FIG. 2. The nutrient solution 9 in container 1 is filled here to the level until the entire small pipe 3 is filled by capillary action. If one then increases the level of the nutrient solution in the container 2, then individual sperm can move through the small pipe 3, and no movement of the nutrient solution as such takes place between the two containers.

Figure 3:
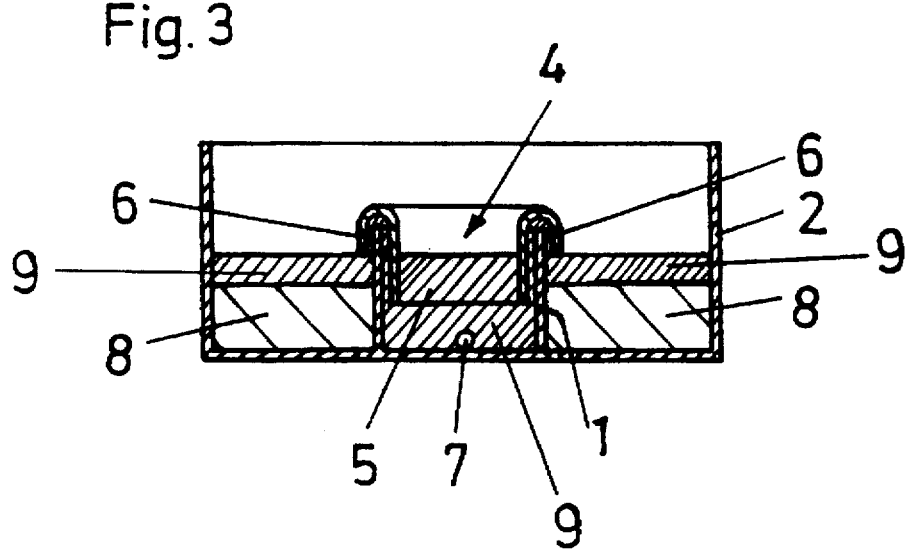

A particularly suitable construction of the capillary conduit is shown in FIG. 3. The two containers 1 and 2 are arranged concentrically inside one another. Nutrient fluid 9 is filled in the container 1, and seminal fluid 8 is placed in the container 2. Then a U-shaped bridge piece or member 4 is placed on the container 1 overlapping an upper edge of the container 1 defined by a wall thereof. The nutrient fluid climbs upward in a gap between the bridge member 4 and the container 1 due to capillary action and slowly covers the seminal fluid 8 until the fluid levels in the containers 1 and 2 have achieved the same height.

The depicted device serves for in vitro fertilization when egg cells 7 are arranged in container 1, which serves to accept the separated sperm cells. Should insemination take place in utero, by contrast, no egg cells are placed in the container 1 and the purified sperm cells are only collected therein.

Figure 4:
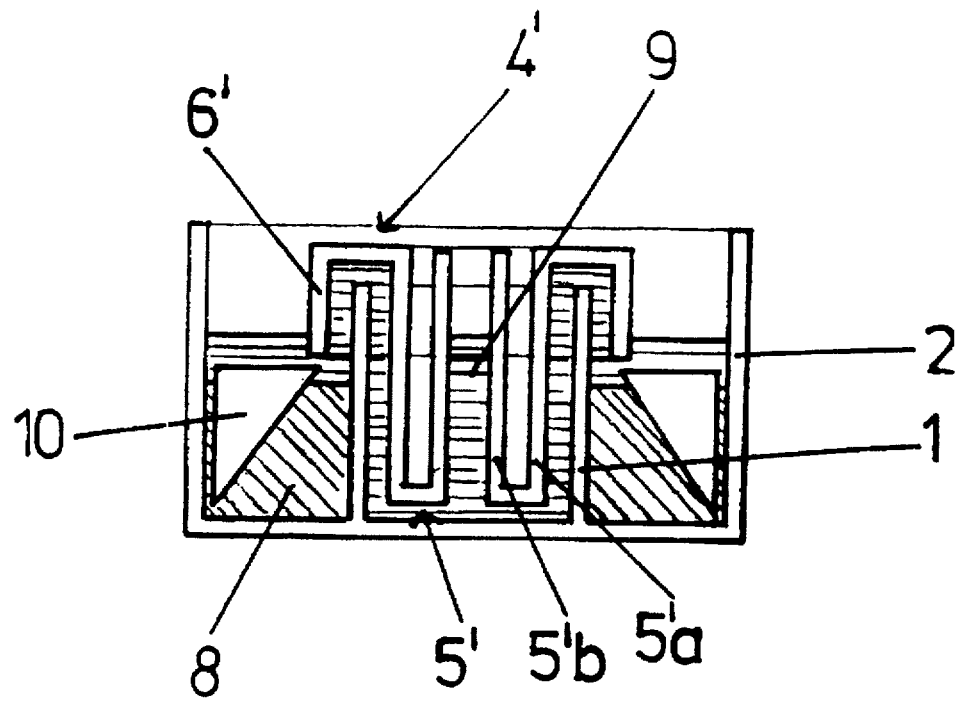

In the exemplary embodiment shown in FIG. 4, both containers 1 and 2 are once again arranged in one another concentrically. An inner portion 5' of a bridge member 4' comprises an outer section 5'a extending substantially to the floor of the container 1 and an adjacent inner section 5'b which defines a smaller volume for accepting the nutrient solution 9 in comparison to the volume of the container 1. Through the reduction of the volume of the nutrient solution for a constant ring surface of the fluid bridge, a sufficiently high concentration of sperm in the nutrient solution 9 is obtained quickly. The path which the sperm must cover is somewhat greater with this form of the bridge member than in the embodiment in FIG. 3.

Figure 5:
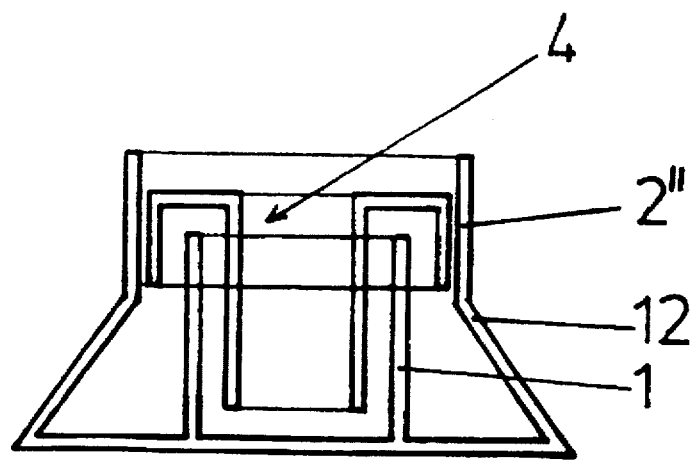

A glass ring 10 is positioned in container 2 of FIG. 4 and forms a suitable space for accepting the seminal fluid 8. Ring 10 tapers upward by and inwardly in a direction to an outer portion 6' of the bridge member 4'. A space designed in this way for accepting seminal fluid also can be achieved by using a container 2" of the form shown in FIG. 5, with a section 12 tapered upwardly and inwardly in the direction of container 1.

In numerous trials it was determined that pure sperm cells can be obtained from severely contaminated fluids with the device of the invention. This is a major advantage in contrast to known processes in which seminal fluid is covered with a nutrient solution and the nutrient solution is sucked up after enrichment with sperm cells (swim-up method). It is expected that the better result can be attributed to the fact that the sperm have a path to cover in accordance with the invention which is significantly larger than the pieces which are covered in comparable times (magnitude 1 hour) by bacteria based on diffusions processes.

I claim:

1. A device for separating sperm cells from seminal fluid, said device comprising:

a first container for accepting seminal fluid;

a second container for accepting sperm cells separated from the seminal fluid;

at least one wall separating interiors of said first and second containers, said at least one wall having an upper edge;

a bridge member having a U-shaped cross-sectional configuration; and said bridge member being positioned to fit over and enclose said upper edge and an upper portion of said at least one wall and to define therewith a gap forming a fluid bridge through which sperm cells may pass from said interior of said first container to said interior of said second container.

2. A device as claimed in claim 1, wherein said gap is of capillary dimensions.

3. A device as claimed in claim 1, wherein said gap has a size of between 0.1 mm and 1 mm.

4. A device as claimed in claim 1, wherein said U-shaped configuration of said bridge member includes a first portion extending into said interior of said first container and a second portion extending into said interior of said second container and having a length greater than said first portion.

5. A device as claimed in claim 4, wherein said second portion includes a first section extending downwardly substantially to a floor of said second container, and a second section extending upwardly from a bottom of said first section and defining within said interior of said second container a smaller volume for accepting nutrient solution.

6. A device as claimed in claim 1, wherein said second container is positioned within said first container, said second container has an outer wall comprising said at least one wall and separating said interiors of said first and second containers, and said bridge member comprises and annular element surrounding said upper portion of said outer wall of said second container.

7. A device as claimed in claim 6, wherein said second container is positioned coaxially within said first container.

8. A device as claimed in claim 6, wherein said U-shaped configuration of said bridge member includes an annular first portion extending into said interior of said first container and an annular second portion extending into interior of said second container and having a length greater than said first portion.

9. A device as claimed in claim 8, wherein said second portion includes a first section extending downwardly substantially to a floor of said second container, and a second section extending upwardly from a bottom of said first section and defining within said interior of said second container a smaller volume for accepting nutrient solution.

10. A device as claimed in claim 1, wherein said interior of said first container is contracted in a direction upwardly and toward said bridge member.

11. A device as claimed in claim 10, wherein said contracted interior is defined by a portion of an outer wall of said first container that is inclined in said direction.

12. A device as claimed in claim 10, wherein said contracted interior is defined by a member positioned within said first container and having a surface that is inclined in said direction.

* * * * *